United States Patent
Ritter et al.

(10) Patent No.: US 7,974,450 B2
(45) Date of Patent: Jul. 5, 2011

(54) METHOD FOR GENERATION OF 3-D X-RAY IMAGE DATA OF A SUBJECT

(75) Inventors: Dieter Ritter, Fürth (DE); Christian Schmidgunst, Straubing (DE)

(73) Assignee: Siemens Aktiengesellschaft, Munich (DE)

( * ) Notice: Subject to any disclaimer, the term of this patent is extended or adjusted under 35 U.S.C. 154(b) by 854 days.

(21) Appl. No.: 11/506,971

(22) Filed: Aug. 17, 2006

(65) Prior Publication Data

US 2007/0053605 A1    Mar. 8, 2007

(30) Foreign Application Priority Data

Aug. 17, 2005  (DE) .................. 10 2005 038 892

(51) Int. Cl.
*G06K 9/40* (2006.01)
*G06K 9/00* (2006.01)
(52) U.S. Cl. ............................ 382/128; 382/260
(58) Field of Classification Search .......... 382/128–132, 382/260; 378/207
See application file for complete search history.

(56) References Cited

U.S. PATENT DOCUMENTS

| | | | | |
|---|---|---|---|---|
| 5,740,268 | A  * | 4/1998 | Nishikawa et al. | 382/132 |
| 5,963,676 | A  * | 10/1999 | Wu et al. | 382/274 |
| 6,078,638 | A  * | 6/2000 | Sauer et al. | 378/4 |
| 6,320,938 | B1 * | 11/2001 | Hopper | 378/156 |
| 6,491,430 | B1 * | 12/2002 | Seissler | 378/207 |
| 2003/0138137 | A1* | 7/2003 | Bojer et al. | 382/132 |
| 2003/0194049 | A1* | 10/2003 | Claus et al. | 378/22 |

FOREIGN PATENT DOCUMENTS

| DE | 103 05 221 | * | 8/2004 |
|---|---|---|---|
| DE | 103 05 221 A1 | | 8/2004 |

OTHER PUBLICATIONS

"Enhanced 3-D-Reconstruction Algorithm for C-Arm Systems Suitable for Interventional Procedures," Wiesent et al., IEEE Trans. on Medical Imaging, vol. 19, No. 5 (May 2000), pp. 391-395.

* cited by examiner

*Primary Examiner* — Vu Le
*Assistant Examiner* — Amara Abdi
(74) *Attorney, Agent, or Firm* — Schiff Hardin LLP

(57) ABSTRACT

In a method for generation of 3D x-ray image data of a subject, a number of initial 2D x-ray images of the subject are acquired from various viewing directions. A number of noise-filtered 2D x-ray images are produced by, for each noise-filtered 2D image, combining at least two of the initial 2D x-ray images with noise filtering. 3D x-ray image data are generated from the noise-filtered 2D x-ray images.

5 Claims, 1 Drawing Sheet

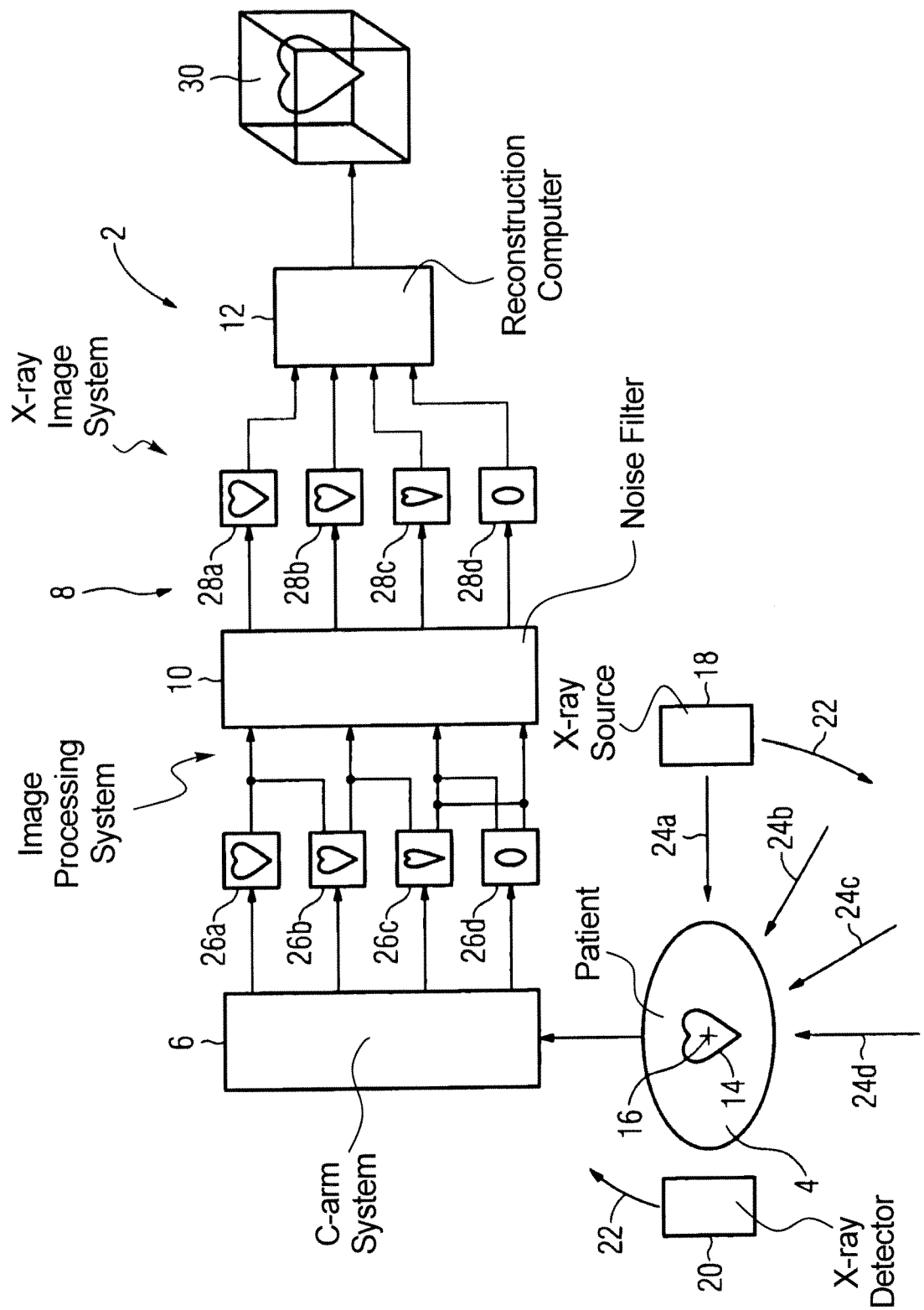

METHOD FOR GENERATION OF 3-D X-RAY IMAGE DATA OF A SUBJECT

BACKGROUND OF THE INVENTION

1. Field of the Invention

The invention concerns a method for generation of 3D x-ray image data of a subject.

2. Description of the Prior Art

X-ray imaging is used in many fields of technology and medicine in order to acquire information about the inside of a subject that is not visible from the outside. Particularly in medicine, patients as subjects are irradiated with x-rays. The patients are normally living people or animals. In addition to the production of conventional 2D x-ray images, the production of 3D image data sets is increasingly gaining importance in medicine.

3D image data sets are generated as reconstructions composed of a number of conventionally-acquired 2D x-ray images. Today both mobile and stationary C-arm systems are used for the creation of such 3D reconstructions or 3D image data sets.

In both systems a sequence of 2D x-ray images is mapped along a predetermined trajectory. For example, given a stationary C-arm angio system several hundred 2D x-ray images of a patient are acquired during a 180° orbital scan. In such an orbital scan, the x-ray source and the x-ray image receiver of the angio system isocentrically orbit the body region of interest on an orbital path.

Due to the geometric calibration of such x-ray systems, which calibration is for the most part implemented in "offline" operation (meaning, for example, directly after the production, thus not in regular operation), the position of every single acquired 2D x-ray image is known relative to the isocenter of the system. The viewing angle, distances and other geometry parameters so determined are entered into and stored in projection matrices belonging to the x-ray system.

A 3D reconstruction volume is calculated from the multiple of 2D x-ray images by suitable methods such as, for example, back-projection. The projection matrices of the system are used for this reconstruction.

In order to obtain a high-quality 3D reconstruction, initially high-quality 2D x-ray images are required that into the corresponding back-projection method. Decisive quality parameters for the 2D x-ray images are, for example, contrast resolution, spatial resolution and the presence of artifacts. A high contrast resolution allows various organs to be differentiated using their brightness in the x-ray image. Artifacts are, for example, pillow or barrel distortions of the image or stripe artifacts, for example caused by ribs or the like moving during the acquisition.

The quality of the contrast resolution is significantly determined by the noise in the 2D x-ray images. The causes of this noise are, among other things, the quantum noise of the x-ray radiation, scatter radiation, spectral sensitivities (triggered, for example, by the "beam hardening effect") and the detector noise in the x-ray image receiver.

In order to obtain a high-quality back projection or a high-quality 3D image data set, it is therefore particularly important to implement an effective noise reduction in the 2D x-ray images.

Various methods are known for this purpose. Noise can be minimized, for example, by a higher x-ray dose. In practice this is avoided as much as possible in order to expose the patient with an optimally low x-ray dose, particularly given the number of 2D x-ray exposures to be generated.

Furthermore it is known to apply a number of filter methods for 2D images (in particular for 2D x-ray images) in this context. Examples for this are line or area filters, morphological operators, frequency filters, median filters, sigma-Lee filters.

For example, from K. Wiesent et al., "Enhanced 3D-Reconstruction Algorithm for C-Arm Systems Suitable for Interventional Procedures", IEEE Trans. on Med. Im., V. 19, N. 5, May 2000, it is known to filter the individual 2D x-ray images together with the inverse point image transformation of the back-projection.

Moreover, filter algorithms are known which are implemented after 3D reconstruction has occurred, thus being implemented directly on the 3D image data set. In the field of MPR visualization there are, for example, filter methods such as thick-MPR or de-streaking.

The goal of any noise suppression is ideally the removal of the noise from the 2D or 3D x-ray image without destroying image information. The corresponding filter methods which are respectively applied to a single 2D x-ray image or to the 3D image data set ultimately lead to a more or less good noise reduction in the 3D x-ray image data.

SUMMARY OF THE INVENTION

An object of the invention is to further improve the generation of 3D x-ray image data of a subject with regard to noise suppression.

The object is achieved by a method for generation of 3D x-ray image data of a subject in which a number of initial 2D x-ray images of the subject are acquired from various viewing directions. A number of noise-filtered images are produced, each from at least two of the initial 2D x-ray images combined with one another with noise filtering. The 3D x-ray image data are generated from the noise-filtered 2D x-ray images.

According to the invention, for noise filtering a filter method or a noise filter is used into which two 2D x-ray images are fed instead of a single 2D x-ray image to be filtered. As before, a single noise-filtered 2D x-ray image is output at the emitted of the noise filter.

Filter methods or filters which form a filtered signal from two input signals correlated with one another are similar to those which generate an output signal from a single input signal. In the present case, the mapping of the same subject in two different first 2D x-ray images represents the correlation between the two images. The usable content, thus the image information in both of the first 2D x-ray images, is thus correlated.

In the inventive method, as outputs of the noise filter, the noise-filtered 2D x-ray images therefore exhibit less noise than images that have previously been used for the 3D reconstruction of 3D x-ray image data, since these have always been generated from a single 2D x-ray image.

Since the 3D x-ray image data are thus generated from better noise-filtered 2D x-ray images compared to previous known methods, the 3D x-ray image data also exhibit less noise.

Such 2D x-ray images that have been acquired from adjacent viewing directions relative to the subject can be selected from the number of initial 2D x-ray images as the 2D x-ray images to be combined with one another.

Filter algorithms that combine two input values into a noise-filtered output value are more effective the more that the usable items of information of the input values are correlated with one another, such that the input values differ only in their noise content.

If the initial 2D x-ray images selected as inputs for noise filtering are acquired from directly-adjacent viewing directions, these contain nearly identical information content; the usable information in the images is thus very strongly correlated. They differ almost solely due to the image noise present in the respective images. Primarily in medical applications of 3D image data generator, 2D x-ray images are often generated that differ in terms of their viewing directions by an angle in the range of less than 1°. The information content of such images that are adjacent with regard to their viewing direction is nearly identical; only the image noise differs.

An image thus arises as a noise-filtered 2D x-ray image whose usable information is nearly completely acquired and whose image noise is simultaneously distinctly better suppressed than given the use of initial 2D x-ray images correlated less strongly with one another as input signals for the noise filtering.

The geometric positions of the viewing directions of the first 2D x-ray images to be combined can be determined, at least relative to one another. If the viewing directions are different, the usable information present in the image is also different (although correlated with one another). However, if it is known in which geometric manner both viewing directions differ from one another (for example their angles relative to one another and the intersection point of the viewing directions), the usable items of information present in both first x-ray images can be mapped to one another. The usable items of information are then correlated with one another in a known manner, which can be taken into account in the noise filtering. The usable information of the initial 2D x-ray images can thus be better retained in the noise-filtered 2D x-ray image, or the image noise can be better removed.

If knowledge about the usable information is present in addition to this, for example in the form of information about the mapped subject that the usable information represents, the items of usable information of both initial 2D x-ray images often can be directly carried over into one another. In the output image (thus the noise-filtered 2D x-ray image), more usable information is thus again obtained, which in turn further improves the quality of the noise-filtered 2D x-ray image and therewith of the x-ray image reconstructions into the 3D image data.

The knowledge of the relative position of the viewing directions relative to one another is thus already advantageous, with knowledge of the absolute position of the viewing directions (for example also relative to the subject) allowing even better correlations of the usable information content of both first 2D x-ray images, and thus an even more beneficial improvement in the quality of the 3D reconstruction.

An x-ray source and/or an x-ray image sensor can be moved along a predetermined trajectory relative to the subject to acquire the initial 2D x-ray images.

For each of the initial 2D x-ray images, the positions of the x-ray source and the x-ray image sensor (and thus also the viewing directions as well as the relative position of the 2D x-ray images relative to on another as well as relative to the subject) can be determined particularly easily by the travel movement on the predetermined trajectory. For example, such information can be determined before the beginning of the generation of the first 2D x-ray images, for example in the installation or manufacture of the system, by a corresponding geometry calibration. The relative or absolute positions mentioned above of, for example, the viewing directions of the 2D x-ray images, are thus known.

The initial 2D x-ray images can be acquired during an orbital scan around the subject in a computed tomography scan. Particularly in computed tomography, for example, up to multiple hundreds of initial 2D x-ray images are acquired during an orbital scan of approximately 180°. The viewing directions of two adjacent 2D x-ray images thus differ by distinctly less than 1°. The correlations of the usable contents of these images are thus particularly large, which leads to the advantages cited above. The inventive method is thus particularly suited for computed tomography.

The initial 2D x-ray images can be combined with one another into the noise-filtered 2D x-ray image using a method based on frequency transformations and discrepancy operators.

Such a method is known from DE 103 05 221 A1. This is particularly suited for the noise filtering by the combination of two images as input values that map the same subject and that have been acquired under geometric conditions that changed in a defined manner. As mentioned, such a method is particularly suitable in the framework of computed tomography.

DESCRIPTION OF THE DRAWING

The single FIGURE schematically illustrates the generation of 3D x-ray image data of the heart of a patient by computed tomography in accordance with the invention.

DESCRIPTION OF THE PREFERRED EMBODIMENTS

The FIGURE shows an x-ray imaging system 2 with a patient 4. The x-ray imaging system 2 has a C-arm system 6 as an x-ray system and an image processing system 8 with a noise filter 10 and a reconstruction computer 12.

The patient 4 is thus placed on a patient bed (not shown) such that his or her heart 14 lies in the isocenter 16 of the C-arm system 6.

For x-ray imaging, an x-ray source 18 and a planar x-ray detector 20 of the C-arm system 6 orbit the isocenter 16 or the patient 4 in the direction of the arrow 22. During this orbital scan, four conventional two-dimensional x-ray images 26a-d are acquired by the C-arm system 6 in four viewing directions, indicated by the arrows 24a-d. Each x-ray image 26a-d shows a representation of the heart 14 in the viewing direction of the arrows 24a-d. In addition to this subject information, each of the four x-ray images 26a-d contains an interference signal (not shown) in the form of image noise that impairs the image quality of the x-ray images 26a-d.

In order to remove this image noise from the x-ray images 26a-d to a large extent, these x-ray images 26a-d are processed in pairs by the noise filter 10 as input images in order to obtain one filtered x-ray image 28a-d per pair as an output image (indicated by the arrows in FIG. 1). The selection of the respective two input images from the group of the x-ray images 26a-d for the noise filter 10 hereby ensues such that two x-ray images 26a-d are selected that are immediately adjacent with regard to their viewing directions, thus the directions of the arrows 24a-d. For example, both input images 26a and 26b whose viewing directions are immediately adjacent in the direction of the arrows 24a and 24b are used for generation of the noise-filtered conventional two-dimensional x-ray image 28a as an output image of the noise filter 10.

The x-ray images 26a-d correspond to the aforementioned initial 2D x-ray images and the x-ray images 28a-d correspond to the noise-filtered 2D x-ray images.

The noise filtering in the noise filter 10 is implemented such that the x-ray image 28a exhibits the same viewing direction in the direction of the arrow 24a of the x-ray image 26a. The x-ray image 26b is thus in fact used together with this for noise filtering, but its viewing direction 24b is not reflected in the x-ray image 28a. For example, the x-ray image 26d forms the basis for generation of the noise-filtered output image 28d, the information or the x-ray image 26c is used as well as a supplementary image for noise filtering. The x-ray image 28d then again has the viewing direction in the direction of the arrow 24d, like the x-ray image 26d.

In a concluding step a three-dimensional reconstruction volume 30 that maps the 3D image data of the heart 14 is calculated from the x-ray images 28a-d with the aid of the reconstruction computer 12.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating 3D x-ray image data of a subject, comprising the steps of:
    with an imaging system, acquiring a plurality of initial 2D x-ray images of the same subject by irradiating the same subject from a plurality of different directions, so each initial 2D x-ray image in said plurality of 2D x-ray images is obtained from a different viewing direction;
    from said plurality of initial 2D x-ray images, forming 2D x-ray image pairs, each 2D x-ray image pair comprising a different subset of at least two of said plurality of 2D x-ray images and supplying the two images in each pair respectively to two inputs of a noise filter;
    in said noise filter, noise-filtering each image pair by combining the respective 2D image therein to produce a single noise-filtered image therefrom, thereby producing a plurality of noise-filtered images respectively from said plurality of image pairs;
    for each noise-filtered image in said plurality of noise-filtered images, assigning a viewing direction thereto that is the respective viewing direction of one of the 2D x-ray images in the pair from which the respective noise-filtered image was produced; and
    in a processor, reconstructing 3D image data from the plurality of noise-filtered images, using the respective viewing directions assigned to the plurality of noise-filtered images, and making said 3D image data available at an output of the processor in a form allowing display of a 3D image of the subject represented by the 3D image data.

2. A method as claimed in claim 1 comprising forming each 2D image group from respective initial 2D x-ray images that were acquired from adjacent viewing directions.

3. A method as claimed in claim 1 comprising acquiring said plurality of initial 2D x-ray images with an x-ray source that irradiates the subject and a radiation detector that detects radiation from the x-ray source attenuated by the subject, and moving at least one of said x-ray source or said radiation detector along a predetermined trajectory relative to the subject to acquire said plurality of initial 2D x-ray images.

4. A method as claimed in claim 3 wherein said predetermined trajectory comprises a computed tomography orbital scan.

5. A method as claimed in claim 1 wherein the step of producing said noise-filtered 2D x-ray images comprises combining the two 2D x-ray images in each pair using frequency transformation and discrepancy operators for noise-filtering.

* * * * *